United States Patent
Zehner et al.

(10) Patent No.: US 11,242,306 B2
(45) Date of Patent: Feb. 8, 2022

(54) CONTINUOUS PREPARATION OF AN OPTICALLY ACTIVE CARBONYL COMPOUND BY ASYMMETRIC HYDROGENATION

(71) Applicant: BASF SE, Ludwigshafen am Rhein (DE)

(72) Inventors: Peter Zehner, Weisenheim am Berg (DE); Oliver Bey, Ludwigshafen am Rhein (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 17/274,142

(22) PCT Filed: Sep. 3, 2019

(86) PCT No.: PCT/EP2019/073456
§ 371 (c)(1),
(2) Date: Mar. 5, 2021

(87) PCT Pub. No.: WO2020/048975
PCT Pub. Date: Mar. 12, 2020

(65) Prior Publication Data
US 2021/0214296 A1 Jul. 15, 2021

(30) Foreign Application Priority Data
Sep. 5, 2018 (EP) .................. 18192756

(51) Int. Cl.
| | |
|---|---|
| *C07C 45/62* | (2006.01) |
| *C07C 29/00* | (2006.01) |
| *B01J 19/00* | (2006.01) |
| *B01J 19/18* | (2006.01) |
| *B01J 31/24* | (2006.01) |
| *C07C 29/17* | (2006.01) |
| *C07C 31/04* | (2006.01) |
| *C07C 33/14* | (2006.01) |
| *C07C 47/21* | (2006.01) |

(52) U.S. Cl.
CPC ........... *C07C 45/62* (2013.01); *B01J 19/0066* (2013.01); *B01J 19/1837* (2013.01); *B01J 31/24* (2013.01); *C07C 29/177* (2013.01); *C07C 31/04* (2013.01); *C07C 33/14* (2013.01); *B01J 2219/00033* (2013.01); *B01J 2531/822* (2013.01); *C07C 47/21* (2013.01)

(58) Field of Classification Search
CPC ......... C07C 45/62; C07C 29/177; B01J 19/00
See application file for complete search history.

(56) References Cited

U.S. PATENT DOCUMENTS

| | | |
|---|---|---|
| 5,756,856 A | 5/1998 | Bueschken et al. |
| 2018/0057437 A1 | 3/2018 | Schelwies et al. |

FOREIGN PATENT DOCUMENTS

EP 0753501 A2 1/1997

OTHER PUBLICATIONS

International Preliminary Reporton Patentability received for PCT Patent Application No. PCT/EP2019/073456, dated Mar. 18, 2021, 15 pages (7 pages of English Translation and 8 pages of Original Document).
International Search Report and Written Opinion received for PCT Patent Application No. PCT/EP19/073456, dated Oct. 1, 2019, 17 pages (8 pages of English Translation and 9 pages of Original Document).

*Primary Examiner* — Sikarl A Witherspoon
(74) *Attorney, Agent, or Firm* — Faegre Drinker Biddle & Reath LLP

(57) ABSTRACT

Process for the continuous production of an optically active carbonyl compound by asymmetric hydrogenation of a prochiral α,β-unsaturated carbonyl compound with hydrogen in the presence of a homogeneous rhodium catalyst that has at least one chiral ligand, wherein a liquid reaction mixture comprising the prochiral α,β-unsaturated carbonyl compound is subjected in a first, backmixed reactor to a gas/liquid two-phase hydrogenation, and the liquid reaction mixture is then further hydrogenated in a second reactor, wherein the prochiral α,β-unsaturated carbonyl compound is employed in the first reactor in a concentration from 3% to 20% by weight. The process allows a high total conversion to the prochiral α,β-unsaturated carbonyl compound.

19 Claims, 3 Drawing Sheets

CONTINUOUS PREPARATION OF AN OPTICALLY ACTIVE CARBONYL COMPOUND BY ASYMMETRIC HYDROGENATION

CROSS-REFERENCE TO RELATED APPLICATIONS

This application is a national stage application (under 35 U.S.C. § 371) of PCT/EP2019/073456, filed Sep. 3, 2019, which claims benefit of European Application No. 18192756.7, filed Dec. 5, 2018, both of which are incorporated herein by reference in their entirety.

The present invention relates to a process for producing optically active carbonyl compounds by asymmetric hydrogenation of a prochiral α,β-unsaturated carbonyl compound with hydrogen in the presence of at least one homogeneous rhodium catalyst that has at least one chiral ligand. In particular, the present invention relates to a process for producing optically active citronellal.

Many optically active aldehydes and ketones are valuable intermediates for the synthesis of highly refined chiral substances of value and active substances and are themselves often sought-after fragrances and aromas.

Menthol is one of the most important aroma chemicals, the majority of which is still isolated from natural sources. A total synthesis approach to the naturally occurring enantiomer L-menthol employs the asymmetric (enantioselective) hydrogenation of geraniol or nerol to optically active citronellal. The optically active citronellal can then be cyclized with acid to L-isopulegol and hydrogenated to L-menthol. There is an ongoing need for optimization of the economic viability of the process and particularly of the initial asymmetric hydrogenation step.

DE 198 54 637 A1 describes a reactor for the continuous performance of gas-liquid, liquid-liquid and gas-liquid-solid reactions, having a downward-oriented jet nozzle and a concentrically arranged guide tube.

EP-A 0 000 315 relates to a process for producing optically active citronellal by the hydrogenation of geranial or neral in the presence of a catalyst complex of rhodium and a chiral phosphine dissolved in the reaction system.

DE 10 2004 049 631 describes a process for producing optically active carbonyl compounds by asymmetric hydrogenation of α,β-unsaturated carbonyl compounds in the presence of optically active transition metal catalysts soluble in the reaction system that have at least one carbon monoxide ligand.

WO 2009/153123 describes a continuous process for the hydrogenation of organic compounds in a multiphase system in the presence of a homogeneous or heterogeneous catalyst in which the process is performed in two stages, the first being performed in a loop reactor with external heat exchanger and the second stage in a bubble-column reactor with limited backmixing.

The present invention relates to a process for the continuous production of an optically active carbonyl compound by asymmetric hydrogenation of a prochiral α,β-unsaturated carbonyl compound with hydrogen in the presence of a homogeneous rhodium catalyst that has at least one chiral ligand, wherein a liquid reaction mixture comprising the prochiral α,β-unsaturated carbonyl compound is subjected in a first, backmixed reactor to a gas/liquid two-phase hydrogenation, and the liquid reaction mixture is then further hydrogenated in a second reactor, wherein the prochiral α,β-unsaturated carbonyl compound is employed in the first reactor in a concentration from 3% to 20% by weight.

It has been found that the reaction rate in the hydrogenation of the prochiral α,β-unsaturated carbonyl compound with hydrogen in the presence of the homogeneous rhodium catalyst at low concentrations of the α,β-unsaturated carbonyl compound initially rises steeply with the concentration of the α,β-unsaturated carbonyl compound, but then at higher concentrations of the α,β-unsaturated carbonyl compound decreases sharply. At high concentrations of the α,β-unsaturated carbonyl compound, the olefinic double bond of the α,β-unsaturated carbonyl compound is presumably able to interact with the rhodium atom of the catalyst, causing reversible inhibition of the catalyst. Such behavior is also referred to as reactant inhibition.

In the process according to the invention, a liquid reaction mixture undergoes reaction in a first, backmixed reactor. The backmixing with the hydrogenation product results in dilution of the α,β-unsaturated carbonyl compound and minimization of reactant inhibition.

The reaction rate can be expressed as the amount of reacted α,β-unsaturated carbonyl compound per unit time, normalized to the molar amount of rhodium atoms. A plot (under the pressure and temperature conditions in the first reactor) against the concentration of the prochiral α,β-unsaturated carbonyl compound shows a maximum $V_{max}$. The prochiral α,β-unsaturated carbonyl compound is preferably employed in the first reactor in a concentration at which the reaction rate is at least 0.8 times $V_{max}$.

In the first reactor, the prochiral α,β-unsaturated carbonyl compound is employed in a liquid-phase concentration of 3% to 20% by weight, preferably 5% to 20% by weight, in particular 5% to 15% by weight, such as 7% to 13% by weight, 8% to 12% by weight, or 9% to 11% by weight, for example 10% by weight. Since the concentration of the prochiral α,β-unsaturated carbonyl compound in the liquid phase is not completely homogeneous, despite the backmixing in the first reactor, the concentration of the prochiral α,β-unsaturated carbonyl compound is considered to be its concentration in the liquid phase at the outlet of the first reactor.

To increase the conversion, the liquid reaction mixture then undergoes further reaction in a second reactor. High concentrations of unreacted prochiral α,β-unsaturated carbonyl compound (hereinafter also referred to as "reactant") in the final reaction mixture result also in high residual concentrations of prochiral α,β-unsaturated carbonyl compound in the catalyst residue, from which the optically active carbonyl compound is separated, e.g. by distillation. The catalyst residue is usually returned to the hydrogenation reaction after a preforming described hereinbelow. High residual concentrations of prochiral α,β-unsaturated carbonyl compound have an adverse effect on the preforming. It is therefore desirable that conversion in the second reactor proceeds largely to completion, minimizing the concentration of unreacted prochiral α,β-unsaturated carbonyl compound.

In the second reactor, the liquid reaction mixture is preferably employed up to a concentration of the prochiral α,β-unsaturated carbonyl compound of less than 5% by weight, in particular less than 3% by weight, such as less than 2% by weight or less than 1% by weight.

The ratio of the reaction volume of the first reactor to the reaction volume of the second reactor is preferably 1:1 to 1:5, in particular 1:2 to 1:4, for example about 1:3.5.

The dwell time profile in a reactor can be represented by the cascade model (see for example Baerns, Hofmann, Renken, "Chemische Reaktionstechnik" [Chemical Reaction Technology]), which describes a real reactor by a theoretical number N ("reactor number") of ideal stirred-tank reactors connected in series. This assumes that the reactors have the same volume and that the reactor volume does not change. Backmixing between the individual reactors is excluded. The reactor number N can be between 1 and infinity, but can only be integer values. The extreme states are N=1 (complete mixing, ideal stirred-tank reactor) or N=∞ (no axial backmixing, ideal flow-tube).

In the process according to the invention, the first reactor preferably has a reactor number within a range from 1 to 3, in particular 1 or 2.

The first reactor is preferably configured as a loop reactor. Examples of loop reactors are tubular reactors having internal and external loops. Such reactors are more particularly described for example in Ullmann's Encyclopedia (Ullmann's Encyclopedia of Industrial Chemistry, Verlag Chemie, Electronic Release 2008, 7th edition, chapters "Stirred-Tank and Loop Reactors" and "Bubble Columns"). A loop reactor usually consists of a vertical, preferably cylindrical, tubular reactor.

The ratio of loop-reactor length to loop-reactor diameter is typically 2:1 to 100:1, preferably 5:1 to 100:1, more preferably 5:1 to 50:1, particularly preferably 5:1 to 30:1.

The reactant is supplied at a point of choice in the tubular reactor, preferably through a jet nozzle, more particularly a jet nozzle arranged above the level of the liquid. The term "jet nozzle" typically refers to a tube that narrows in the direction of flow. The jet nozzle causes mixing in the first reactor.

The volume-specific power input into the first reactor is preferably 0.5 to 5 kW/m$^3$, for example 1.0 to 4 kW/m$^3$ or 1.5 to 3 kW/m$^3$. The volume-specific power input can be determined as the product of the pressure differential across the jet nozzle and volume flow through the nozzle.

The jet nozzle can be configured as a single-substance or two-substance nozzle. In the case of a single-substance nozzle, only the liquid reaction mixture is injected, with the hydrogen injected at another point of choice but preferably in the lower region of the reactor. The advantage of this design is the simple construction of such a single-substance nozzle. Injection of hydrogen in the lower region of the reactor advantageously promotes the circulation of the reaction mixture in the reactor. With the two-substance nozzle, the hydrogen is supplied together with the liquid reaction mixture and dispersed.

In a preferred embodiment, the reaction mixture is metered in downwards via a single-substance jet nozzle present at the top of the reactor. Hydrogen collects in the gas space above the liquid level in the reactor. The jet from the nozzle falls through the gas space and hits the hydrogen gas on entry into the liquid phase, causing the gas to dissipate into bubbles and undergo dispersion in the liquid phase.

The loop reactor is generally configured as a tubular reactor with an external circuit (external loops). In a loop reactor with an external circuit, there is generally a draw at a point of choice in the reactor, preferably in the lower region of the reactor, via which the reaction mixture is fed back to the jet nozzle in an external circuit by means of a conveyor element. The conveyor element is preferably a pump and the external circuit is therefore typically referred to as a pumped-circulation circuit.

Examples of pumps are centrifugal pumps or rotary piston pumps, such as rotary lobe pumps, rotary vane pumps, circumferential piston pumps or gear pumps. It is particularly preferable to employ centrifugal pumps as the conveyor element.

The first reactor is preferably configured as a loop reactor with an external circuit, a heat exchanger being present in the external circuit. Such a reactor is referred to in the context of this invention as a loop reactor with external heat exchanger.

The heat exchanger is for example a shell-and-tube heat exchanger, double shell-and-tube heat exchanger, plate heat exchanger or spiral heat exchanger. At reactor design pressures below 100 bar it is preferable to use a shell-and-tube heat exchanger, whereas at higher pressures it is preferable to use one or more double shell-and-tube heat exchangers connected in series.

The loop reactor with external heat exchanger is typically operated such that a portion of the reaction mixture from the reactor is conveyed through the external pumped-circulation circuit containing the external heat exchanger, thus cooling the reaction mixture conveyed through the heat exchanger. The external pumped circulation normally causes the reaction mixture in the first reaction stage to be vigorously mixed and recirculated, with the result that the dwell time in the first stage typically corresponds to that of a continuously backmixed stirred-tank reactor (CSTR).

The reaction mixture is finally returned to the reactor by means of the jet nozzle. Typically, fresh reactants and fresh catalyst solution are introduced into the pumped-circulation circuit and, together with the stream already present in the pumped-circulation circuit, supplied to the reactor as reaction mixture.

In a preferred embodiment, the loop reactor is designed such that a so-called internal loop flow develops in addition to the external circuit. In a loop reactor with internal loop flow, a concentric, preferably cylindrical guide tube is normally arranged in the interior of the tubular reactor, this guide tube essentially spanning the entire length of the tubular reactor except for the reactor ends.

The guide tube is normally configured as a simple tube. The length-to-diameter ratio of the guide tube is generally 5:1 to 100:1, preferably 5:1 to 50:1.

The diameter of the guide tube is less than the diameter of the tubular reactor. The ratio of guide-tube diameter to tubular-reactor diameter is generally 0.3:1 to 0.9:1, preferably 0.5:1 to 0.7:1. The space between the guide tube and the reactor wall is generally referred to as the annular space.

The jet nozzle is usually arranged such that the gas/liquid jet generated by the jet nozzle is directed into the guide tube. The jet nozzle is preferably arranged above the upper end of the guide tube. The nozzle tip is located above the level of the liquid and does not dip into the liquid phase. The gas/liquid jet generated by the jet nozzle causes a downward flow in the guide tube (downstream column) that, after exiting the guide tube, is deflected such that the liquid in the annular space between the guide tube and the reactor wall flows back up toward the jet nozzle (upflow column). This normally gives rise to an internal loop flow. The ratio of volume flows of the internal loop flow to the reaction mixture in external pumped circulation is preferably 2 to 30:1, more preferably 5 to 20:1.

At least part of the reaction mixture is supplied from the first reactor to the second reactor. Backmixing in the second reactor is preferably limited such that the dwell time distribution in this second reactor approximates to that of a tubular reactor. This defined liquid dwell time allows the reactant to undergo almost complete conversion. The second reactor preferably has a reactor number of more than 4, in particular more than 5 or more than 6.

The second reactor usually consists of a vertical, preferably cylindrical, tubular reactor. The ratio of reactor length to reactor diameter is typically 2:1 to 100:1, preferably 5:1 to 50:1, more preferably 7:1 to 25:1.

In a section of the second reactor located at the exit from the second reactor, the hydrogenation takes place preferably as a liquid single-phase reaction, i.e. in the section located at the exit from the second reactor there is no dispersed gas phase and the hydrogenation takes place exclusively with hydrogen dissolved in the liquid phase. Since the hydrogenation turnovers toward the exit from the second reactor are low, the concentration of dissolved hydrogen is sufficient. The absence of a discrete gas phase toward the exit from the second reactor means that the liquid holdup in the second reactor can be increased and the dwell time of the liquid phase in the second reactor extended. Since the hydrogenation takes place in the liquid phase, this makes optimal use of the reaction space. The section of the second reactor operated in liquid single-phase accounts for preferably 30 to 50% of the total volume of the second reactor.

Backmixing in the second reactor is preferably limited by internals. The fitting of such devices generally limits the circulation and thus the backmixing of gas and liquid.

The limiting of backmixing in the second reactor may be achieved through fitting various internals. In a preferred embodiment, the limiting of backmixing is effected by fitting a plurality of fixed trays in the tubular reactor. This gives rise to individual segments ("compartments") having defined reaction volumes between the individual trays. Each of the individual segments generally acts as an individual, backmixed stirred-tank reactor. As the number of consecutive individual segments increases, the dwell time distribution of such a cascade generally approaches the dwell time of a tubular reactor. The number of individual segments thus formed is preferably 2 to 20, more preferably 2 to 10, particularly preferably 3 to 6. The trays used here are preferably liquid-permeable trays. It is particularly preferable when the trays are perforated metal sheets.

In order to ensure sufficient hydrogen saturation, hydrogen gas undergoes dispersion in the liquid reaction mixture preferably in a section of the second reactor located toward the entrance to the second reactor, e.g. in the first individual segment of the second reactor.

The section of the second reactor located at the entrance to the second reactor is for this purpose preferably designed as a loop reactor with an external circuit. The dispersion of hydrogen into the section is preferably effected through a jet nozzle. The jet nozzle can be configured as a single-substance or two-substance nozzle. A draw is present at a point of choice in the section via which the reaction mixture is fed back to the jet nozzle in an external circuit by means of a conveyor element. The hydrogen can be supplied together with the liquid reaction mixture or can be metered into the section located at the entrance to the second reactor at a point of choice.

The loop reactor with an external circuit preferably comprises a heat exchanger and is operated in such a way that the reaction mixture fed out of the reactor through the external pumped-circulation circuit is cooled by the heat exchanger.

In a preferred embodiment, the reaction mixture is metered in downwards via a single-substance jet nozzle present at the top of the second reactor. The jet from the nozzle falls through the gas space and hits the gas on entry into the liquid phase, causing the gas to dissipate into bubbles and undergo dispersion in the liquid phase.

The number of individual segments in the second reactor is preferably 2 to 10, more preferably 2 to 10, particularly preferably 3 to 6. The volume of the first individual segment, in which hydrogen gas is dispersed in the liquid reaction mixture, is preferably 30 to 70% based on the total volume of the second reactor. The second segment to the last individual segment of the second reactor are preferably operated in liquid single-phase; the second segment to the last individual segment of the second reactor then preferably accounts for 30 to 70% of the total volume of the second reactor.

The first reactor and the second reactor are preferably arranged as two spatially separate apparatuses connected to one another via pipelines.

In other embodiments, both reactors can be arranged in one apparatus (hydrogenation reactor). In this preferred embodiment, the hydrogenation reactor is configured as a long, cylindrical tube (tall cylindrical construction).

A prochiral α,β-unsaturated carbonyl compound can form a chiral center through an addition reaction at the olefinic double bond. The double bond here bears four different substituents. The prochiral α,β-unsaturated carbonyl compound is preferably selected from compounds of the general formula (I)

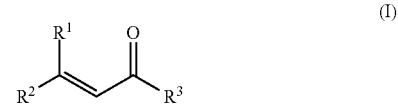

where
$R^1$, $R^2$ are different from one another and are each an unbranched, branched or cyclic hydrocarbon radical having 1 to 25 carbon atoms that is saturated or has one or more unconjugated ethylenic double bonds and that is unsubstituted or bears one or more identical or different substituents selected from $OR^4$, $NR^{5a}R^{5b}$, halogen, $C_6$-$C_{10}$ aryl and heteroaryl having 5 to 10 ring atoms,
$R^3$ is hydrogen or an unbranched, branched or cyclic hydrocarbon radical having 1 to 25 carbon atoms that is saturated or has one or more unconjugated ethylenic double bonds and that is unsubstituted or bears one or more identical or different substituents selected from $OR^4$, $NR^{5a}R^{5b}$, halogen, $C_6$-$C_{10}$ aryl and heteroaryl having 5 to 10 ring atoms,
or
$R^3$ jointly with either of the radicals $R^1$ or $R^2$ may also represent a 3- to 25-membered alkylene group wherein 1, 2, 3 or 4 nonadjacent $CH_2$ groups may be replaced by O or N—$R^{5c}$, wherein the alkylene group is saturated or has one or more unconjugated ethylenic double bonds and wherein the alkylene group is unsubstituted or bears one or more identical or different substituents selected from $OR^4$, $NR^{5a}R^{5b}$, halogen, $C_1$-$C_4$ alkyl, $C_6$-$C_{10}$ aryl and heteroaryl having 5 to 10 ring atoms, wherein two substituents may also jointly represent a 2- to 10-membered alkylene group, wherein the 2- to 10-membered alkylene group is saturated or has one or more unconjugated ethylenic double bonds and wherein the 2- to 10-membered alkylene group is unsubstituted or bears one or more identical or different substituents selected from $OR^4$, $NR^{5a}R^{5b}$, halogen, $C_6$-$C_{10}$ aryl and heteroaryl having 5 to 10 ring atoms;
where $R^4$ is hydrogen, $C_1$-$C_6$ alkyl, $C_6$-$C_{10}$ aryl, $C_6$-$C_{14}$ aryl-$C_1$-$C_{10}$ alkyl, or $C_1$-$C_{10}$ alkyl-$C_6$-$C_{14}$ aryl;

$R^{5a}$, $R^{5b}$ are each independently hydrogen, $C_1$-$C_6$ alkyl, $C_6$-$C_{10}$ aryl, $C_6$-$C_{14}$ aryl-$C_1$-$C_{10}$ alkyl or $C_1$-$C_{10}$ alkyl-$C_6$-$C_{14}$ aryl or $R^{5a}$ and $R^{5b}$ may also jointly represent an alkylene chain having 2 to 5 carbon atoms, which may be interrupted by N or O; and $R^{5c}$ is hydrogen, $C_1$-$C_6$ alkyl, $C_6$-$C_{10}$ aryl, $C_6$-$C_{14}$ aryl-$C_1$-$C_{10}$ alkyl, or $C_1$-$C_{10}$ alkyl-$C_6$-$C_{14}$ aryl.

In preferred embodiments, the prochiral α,β-unsaturated carbonyl compound is selected from compounds of the general formulas (Ia) and (Ib)

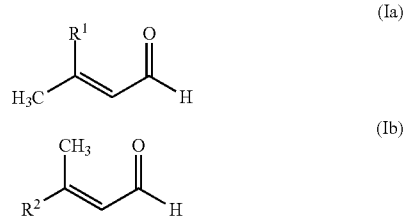

where $R^1$, $R^2$ are each an unbranched or branched hydrocarbon radical having 2 to 25 carbon atoms that is saturated or has 1, 2, 3, 4 or 5 unconjugated ethylenic double bonds.

A particularly preferred embodiment relates to a process for producing optically active citronellal of the formula (III)

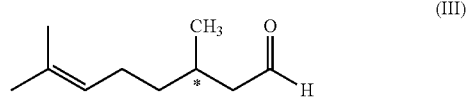

where * denotes the asymmetric center;

by asymmetric hydrogenation of geranial of the formula (Ia-1) or of neral of the formula (Ib-1)

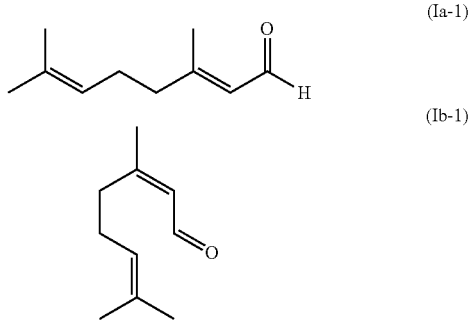

or of a mixture comprising neral and geranial. A mixture comprising neral and geranial is known as citral.

The optically active citronellal of the formula (III) thus obtainable may be subjected to a cyclization to afford optically active isopulegol and the optically active isopulegol hydrogenated to afford optically active menthol.

Through the process according to the invention it is possible to provide optically active carbonyl compounds, in particular optically active aldehydes, in high yields and high enantiomeric excesses. The desired asymmetrically hydrogenated compounds are typically obtained in an enantiomeric excess of at least 80% ee, often with an enantiomeric excess of about 85% to about 99% ee. A point to note here is that the maximum achievable enantiomeric excess may be dependent on the purity of the substrate used, more particularly in respect of the isomeric purity of the double bond to be hydrogenated. Accordingly, particularly suitable starting substances are those in which the isomer ratio is at least about 90:10, preferably at least about 95:5, with regard to the E/Z double bond isomers.

The production process according to the invention is carried out in the presence of an optically active rhodium catalyst that is soluble in the reaction mixture and has at least one optically active ligand. Catalysts of this kind are obtainable for example by reacting a suitable rhodium compound that is soluble in the reaction mixture with an optically active ligand having at least one phosphorus and/or arsenic atom.

Examples of rhodium compounds that can be used according to the invention are: $RhCl_3$, $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$, $Rh_6(CO)_{16}$, where "acac" is an acetylacetonate ligand and "cod" is a cyclooctadiene ligand.

The catalyst concentration in the reaction mixture is preferably 0.001 to 1 mol %, in particular 0.002 to 0.5 mol %, particularly preferably 0.005 to 0.2 mol %, based on the amount of prochiral α,β-unsaturated carbonyl compound in the reaction mixture calculated as rhodium atoms present in the catalyst.

The recited rhodium compounds are contacted with a further compound that is optically active, preferably essentially enantiomerically pure (i.e. having an enantiomeric excess of at least about 99%), and has at least one phosphorus and/or arsenic atom, preferably at least one phosphorus atom. This compound referred to as the chiral ligand forms, in the reaction mixture or in the preforming mixture with the employed rhodium compound, the rhodium catalyst to be used according to the invention.

Particular preference is given to chiral ligands that have two phosphorus atoms and form chelate complexes with rhodium.

Chiral ligands suitable in the context of the present invention include compounds such as those described for example in: I. Ojima (ed.), Catalytic Asymmetric Synthesis, Wiley-VCh, 2nd edition, 2000 or in E. N. Jacobsen, A. Pfaltz, H. Yamamoto (eds.), Comprehensive Asymmetric Catalysis, 2000, Springer or in W. Tang, X. Zhang, Chem. Rev. 2003, 103, 3029-3069.

Preferred ligands are chiral bidentate bisphosphine ligands, particularly those of the general formulas (IV) to (VI)

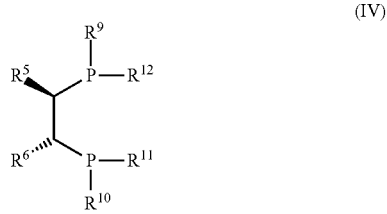

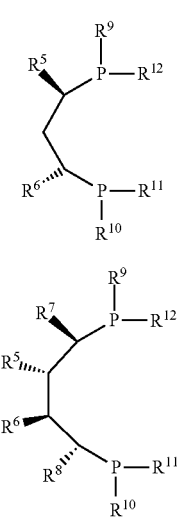

(V)

(VI)

where $R^5$, $R^6$ are each independently an unbranched, branched or cyclic hydrocarbon radical having 1 to 20 carbon atoms that is saturated or may have one or more, generally 1 to about 4, unconjugated ethylenic double bonds and that is unsubstituted or may bear one or more, generally 1 to 4, identical or different substituents selected from $OR^{13}$, $NR^{14}R^{15}$, halogen, $C_6$-$C_{10}$ aryl and $C_3$-$C_9$ heteroaryl, or $R^5$ and $R^6$ may jointly represent a 2- to 10-membered alkylene group or a 3- to 10-membered cycloalkylene group, in which 1, 2, 3 or 4 nonadjacent CH groups may be replaced by O or N—$R^{13}$, wherein the alkylene group and the cycloalkane group are saturated or have one or two unconjugated ethylenic double bonds and wherein the alkylene group and the cycloalkylene group are unsubstituted or bear one or more identical or different substituents selected from $C_1$-$C_4$ alkyl;

$R^7$, $R^8$ are each independently hydrogen or straight-chain or branched $C_1$-$C_4$ alkyl and $R^9$, $R^{10}$, $R^{11}$, $R^{12}$ are identical or different and are $C_6$-$C_{10}$ aryl that is unsubstituted or bears one or more substituents selected from $C_1$-$C_6$ alkyl, $C_3$-$C_6$ cycloalkyl, $C_6$-$C_{10}$ aryl, $C_1$-$C_6$ alkoxy and amino;

$R^{13}$, $R^{14}$, R are each independently hydrogen, $C_1$-$C_4$ alkyl, $C_6$-$C_{10}$ aryl, $C_7$-$C_{12}$ aralkyl or $C_1$-$C_{12}$ alkylaryl, where $R^{14}$ and $R^{15}$ may also jointly represent an alkylene chain having 2 to 5 carbon atoms, which may be interrupted by N or O.

In the formulas (IV), (V), and (VI), the variables are in particular as follows:

$R^5$, $R^6$ are each independently $C_1$-$C_4$ alkyl or $R^5$ and $R^6$ jointly represent a $C_3$-$C_5$ alkanediyl radical, $C_3$-$C_7$ alkenediyl radical, $C_5$-$C_7$ cycloalkanediyl radical or a $C_5$-$C_7$ cycloalkenediyl radical, wherein the four above-mentioned radicals are unsubstituted or bear one or more identical or different substituents selected from $C_1$-$C_4$ alkyl;

$R^7$, $R^8$ are each independently hydrogen or $C_1$-$C_4$ alkyl;

$R^9$, $R_{10}$, $R^{11}$, $R^{12}$ are each phenyl.

Chiral, bidentate bisphosphine ligands particularly preferred on account of their ready availability are compounds obtainable under the name "chiraphos" of the formula:

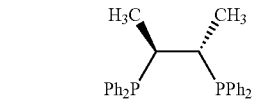

The chiral ligands are advantageously used in an amount of about 0.9 to about 10 mol, preferably about 1 to about 4 mol, per mol of rhodium compound used. The optically active rhodium catalyst soluble in the reaction mixture is conveniently generated in situ by reacting an achiral rhodium compound with a chiral bidentate bisphosphine ligand before or during the hydrogenation. In this context the term "in-situ" is understood as meaning that the catalyst is generated immediately before or at the start of the hydrogenation. The catalyst is preferably generated before the hydrogenation.

It has been found that the presence of monodentate ligands can increase the activity of the catalyst. A preferred embodiment of the process according to the invention employs compounds of the formula (II)

(II)

$$R^{17}\overset{\overset{R^{16}}{|}}{\underset{}{P}}Z$$

where Z in the formula (II) is a $CHR^{18}R^{19}$ group and where the variables $R^{16}$, $R^{17}$, $R^{18}$, $R^{19}$ are independently, and in particular jointly, as follows:

$R^{16}$, $R^{17}$: are identical or different and are phenyl that is unsubstituted or bears 1, 2 or 3 substituents selected from methyl and methoxy, where $R^{16}$ and $R^{17}$ are each in particular unsubstituted phenyl;

$R^{18}$ is $C_1$ to $C_4$ alkyl, in particular methyl;

$R^{19}$ is $C_1$ to $C_4$ alkyl bearing a $P(=O)R^{19a}R^{19b}$ group and in particular a $CH_2$—$P(=O)R^{19a}R^{19b}$ or $CH(CH_3)$—$P(=O)R^{19a}R^{19b}$ group;

where $R^{19a}$, $R^{19b}$: are identical or different and are phenyl that is unsubstituted or bears 1, 2 or 3 substituents selected from methyl and methoxy, where $R^{19a}$ and $R^{19b}$ are particularly preferably each unsubstituted phenyl.

In this preferred embodiment of the process according to the invention, particular preference is given to using a compound of the formula (II), where $R^{16}$, $R^{17}$: are unsubstituted phenyl;

$R^{18}$ is methyl;

$R^{19}$ is a $CH(CH_3)$—$P(=O)R^{19a}R^{19b}$ group, where $R^{19a}$ and $R^{19b}$ are each unsubstituted phenyl.

This is the compound (2-(diphenylphosphoryl)-1-methylpropyl)diphenylphosphane (chiraphos monooxide) encompassing the (R,R) enantiomer (=(R,-chiraphos monooxide) and the (S,S) enantiomer (=(S,S)-chiraphos monooxide) and mixtures of ((R,R)-chiraphos monooxide and (S,S)-chiraphos monooxide.

When the radicals $R^{18}$ and $R^{19}$ in the general formula (II) are different, the carbon atom bearing the radicals $R^{18}$ and $R^{19}$ may have an (R) or (S) configuration. These compounds of the general formula (II) may be in the form of pure (R) or pure (S) stereoisomers or as mixtures thereof. The pure (R) and (S) stereoisomers are normally used in such instances, but any stereoisomer mixtures are also suitable for use in the present process.

A pure stereoisomer is here and hereinbelow understood as meaning chiral substances in which the desired stereoisomer is present in an enantiomeric excess (ee) of at least 80% ee, in particular at least 90% ee, and especially at least 95% ee.

More particularly, the chiral ligand used is chiraphos and the monodentate compound used is (2-(diphenylphosphoryl)-1-methylpropyl)diphenylphosphane (chiraphos monooxide). For example, the chiral ligand used is R-chiraphos and the monodentate compound used is (R,R)-chiraphos monooxide and/or (S,S)-chiraphos monooxide. Alternatively, the chiral ligand used is S-chiraphos and the monodentate compound used is (R,R)-chiraphos monooxide and/or (S,S)-chiraphos monooxide.

According to the invention the compound of the formula (II) is normally used in an amount of 0.01 to 1 mol, preferably 0.02 to 0.8 mol, more preferably 0.03 to 0.7 mol and in particular in an amount of 0.04 to 0.6 mol per mol rhodium.

Further embodiments of the rhodium catalyst and of the monodentate ligand are described in US 2018/0057437 A1, WO 2006/040096 A1, and WO 2008/132057 A1.

The hydrogen used for the hydrogenation is generally used in a relatively large stoichiometric excess of 1 to 10 times, preferably 1.1 to 5 times, the stoichiometrically necessary amounts. It can be fed back into the reaction as cycle gas. The hydrogen used is generally of technical grade purity. The hydrogen may also be used in the form of a hydrogen-comprising gas, i.e. in mixtures with other inert gases such as nitrogen, helium, neon, argon or carbon dioxide. Reformer offgases, refinery gases etc. may for example be used as hydrogen-comprising gases. Preference is however given to using pure hydrogen or essentially pure hydrogen in the process.

The asymmetric hydrogenation according to the invention is advantageously carried out at a pressure of about 2 to about 200 bar, in particular of about 10 to about 100 bar, especially of about 60 to about 100 bar and a temperature of generally about 0° C. to about 100° C., preferably about 0° C. to about 30° C., in particular at about 10° C. to about 30° C.

The choice of solvent to be used for carrying out the asymmetric hydrogenation of the invention is of low importance. Examples of suitable solvents or dissolution media that are inert under the reaction conditions include ethers, tetrahydrofuran, methyltetrahydrofuran, toluene, xylenes, chlorobenzene, octadecanol, biphenyl ether, Texanol, Marlotherm, Oxoöl 9N (hydroformylation products from isomeric octenes, BASF SE), citronellal, and the like. It is also possible to use as the dissolution medium the hydrogenation product or any high-boiling by-products formed in the reaction. It is particularly advantageous to carry out the asymmetric hydrogenation in the same solvent as any preforming carried out optionally beforehand.

In a preferred embodiment of the process according to the invention, the catalyst is prior to the hydrogenation pretreated with a gas mixture comprising carbon monoxide and hydrogen and/or the asymmetric hydrogenation is carried out in the presence of carbon monoxide additionally supplied to the reaction mixture.

This means that the rhodium catalyst used, which is soluble in the reaction mixture, i.e. homogeneous, is either pretreated prior to the asymmetric hydrogenation with a gas mixture comprising carbon monoxide and hydrogen (i.e. "preforming" is carried out) or the asymmetric hydrogenation is carried out in the presence of carbon monoxide additionally supplied to the reaction mixture or preforming is carried out followed by asymmetric hydrogenation carried out in the presence of carbon monoxide additionally supplied to the reaction mixture.

The rhodium catalysts used in this preferred embodiment and soluble in the reaction mixture may therefore—at least in a form that participates in the catalytic cycle or in a precursor upstream of the actual catalytic cycle—have at least one CO ligand, it being immaterial whether this catalyst form having at least one CO ligand constitutes the actual catalytically active form of the catalyst. To stabilize catalyst forms potentially having CO ligands, it can be advantageous to additionally supply carbon monoxide to the reaction mixture during the hydrogenation.

In this preferred embodiment, the mentioned pretreatment of the catalyst precursor is carried out with a gas mixture comprising 20% to 90% by volume of carbon monoxide, 10% to 80% by volume of hydrogen, and 0% to 5% by volume of other gases, the sum of the mentioned proportions by volume being 100%, and at a pressure of 5 to 100 bar. In addition, excess carbon monoxide is removed from the catalyst thus obtained before use in the asymmetric hydrogenation. The term excess carbon monoxide is to be understood as meaning carbon monoxide present in the obtained reaction mixture in gaseous or dissolved form and not bonded to the rhodium catalyst or to the precursor thereof. The excess carbon monoxide not bonded to the catalyst is thus at least largely removed, i.e. to an extent such that any residual amounts of dissolved carbon monoxide cause no appreciable interference in the subsequent hydrogenation. This is typically ensured when about 90%, preferably about 95% or more, of the carbon monoxide used for preforming is removed. The excess carbon monoxide is preferably completely removed from the catalyst obtained through preforming.

The excess carbon monoxide may be removed in various ways from the catalyst obtained or from the reaction mixture comprising the catalyst. The catalyst or catalyst-comprising mixture obtained through preforming is preferably depressurized to a pressure of up to about 5 bar (absolute), preferably, especially when preforming is carried out within a pressure range from 5 to 10 bar, to a pressure of less than 5 bar (absolute), preferably to a pressure within a range from about 1 bar to about 5 bar, preferably 1 to less than 5 bar, particularly preferably to a pressure within a range from 1 to 3 bar, very particularly preferably to a pressure within a range from about 1 to about 2 bar, especially preferably to normal pressure, with the result that gaseous, unbonded carbon monoxide escapes from the preforming product. The abovementioned depressurization of the preformed catalyst may be carried out for example using a high-pressure separator such as those known per se by those skilled in the art. Such separators, in which the liquid is in the continuous phase, are described for example in: Perry's Chemical Engineers' Handbook, 1997, 7th ed., McGraw-Hill, pp. 14.95 and 14.96; the prevention of possible droplet entrainment is described on pages 14.87 to 14.90. Depressurization of the preformed catalyst may be carried out in a one-stage or two-stage process until the desired pressure within a range from 1 bar to about 5 bar is attained, this being typically accompanied by a fall in temperature to 10° C. to 40° C. Excess carbon monoxide may alternatively be removed by so-called stripping of the catalyst or catalyst-comprising mixture with a gas, advantageously with a gas that is inert under the reaction conditions. The term stripping is understood by those skilled in the art as meaning the introduction of a gas into the catalyst or catalyst-comprising reaction mixture, for example as described in W. R. A.

Vauck, H. A. Müller, Grundoperationen chemischer Verfahrenstechnik [Basic operations in chemical process technology], Deutscher Verlag für Grundstoffchemie Leipzig, Stuttgart, 10th edition, 1984, page 800. Examples of inert gases suitable therefor include: hydrogen, helium, neon, argon, xenon, nitrogen and/or $CO_2$, preferably hydrogen, nitrogen, argon.

The asymmetric hydrogenation is preferably then carried out with hydrogen having a carbon monoxide content within a range from 50 to 3000 ppm, in particular within a range from 100 to 2000 ppm, especially within a range from 200 to 1000 ppm, and very especially within a range from 400 to 800 ppm.

If preforming the rhodium catalyst, the selected rhodium compound and the selected chiral ligand are typically dissolved in a suitable solvent or dissolution medium that is inert under the reaction conditions, for example ether, tetrahydrofuran, methyltetrahydrofuran, toluene, xylenes, chlorobenzene, octadecanol, biphenyl ether, Texanol, Marlotherm, Oxoöl 9N (hydroformylation products of isomeric octenes, BASF Aktiengesellschaft), citronellal, and the like. It is also possible to use as the dissolution medium the hydrogenation product or any high-boiling by-products formed in the reaction. The resulting solution, advantageously in a suitable pressure reactor or autoclave, is pressurized with a gas mixture comprising hydrogen and carbon monoxide at a pressure of typically about 5 to about 350 bar, preferably of about 20 to about 200 bar, and more preferably of about 50 to about 100 bar. Preforming is preferably carried out using a gas mixture comprising about 30% to 99% by volume of hydrogen,
1% to 70% by volume of carbon monoxide, and
0% to 5% by volume of other gases, the sum of the proportions by volume being 100%.

A gas mixture particularly preferred for preforming is so-called syngas, which typically comprises 35% to 55% by volume of carbon monoxide in addition to hydrogen and traces of other gases.

The preforming of the catalyst is typically performed at temperatures of about 25° C. to about 100° C., preferably at about 40° C. to about 80° C. Preforming is typically completed after about 1 h to about 24 h, often after about 1 h to about 12 h. The preforming optionally carried out is followed, according to the invention, by the asymmetric hydrogenation of the selected substrate. After a preceding preforming, the selected substrate can usually be carried out with or without supply of additional carbon monoxide. If no preforming is carried out, the asymmetric hydrogenation according to the invention can be carried out either in the presence of carbon monoxide supplied to the reaction system or without the supply of carbon monoxide. It is advantageous when preforming as described is carried out and additional carbon monoxide is added to the reaction mixture during the asymmetric hydrogenation.

If carbon monoxide is supplied to the reaction system, the supply may be undertaken in various ways. For example the carbon monoxide may be mixed into the hydrogen used for the asymmetric hydrogenation or else directly introduced into the reaction solution in gaseous form. The carbon monoxide is preferably mixed into the hydrogen used for the asymmetric hydrogenation.

The reaction product can be removed from the reaction mixture by methods known per se to those skilled in the art, for example by distillation and/or flash evaporation, and the residual catalyst used in further reactions, optionally after renewed preforming. In the context of the preferred embodiment it is advantageous when no solvent is added and when the described conversions are carried out in the substrate undergoing reaction/in the product and optionally in high-boiling by-products as the dissolution medium. Particular preference is given to a continuous reaction mode with reuse/recycling of the homogeneous catalyst stabilized according to the invention.

The invention is more particularly elucidated by the accompanying figures and by the example that follows.

Figure 1:
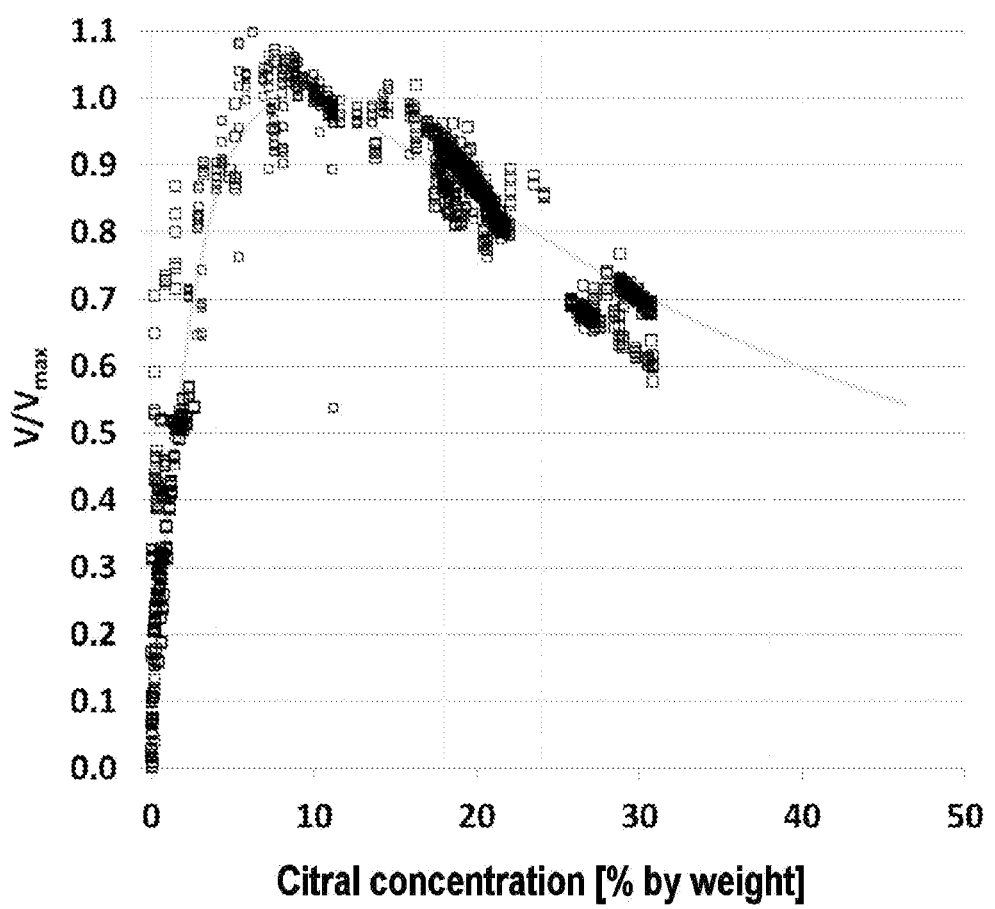
FIG. 1 shows a plot of the reaction rate (relative to the maximum reaction rate) of the hydrogenation of citral in the presence of a chiraphos rhodium catalyst as a function of the citral concentration.

The data shown in FIG. 1 were obtained in a jet loop reactor in which different conversions were achieved through different catalyst loads. The difference between the amount of citral entering and exiting the reactor was related here to the mass of rhodium in the reactor and plotted via the citral concentration in the outflow from the reactor. This reaction rate thus determined was normalized with the maximum reaction rate.

It can be seen from FIG. 1 that the reaction rate of the citral hydrogenation increases hyperbolically with the citral concentration at low citral concentrations, but then decreases sharply at higher citral concentrations. The maximum reaction rate $V_{max}$ is attained at a citral concentration of about 9% by weight. Reaction rates equal to or greater than 0.8 times $V_{max}$ are attained in the concentration range from about 5% to 20% by weight of citral.

Figure 2:
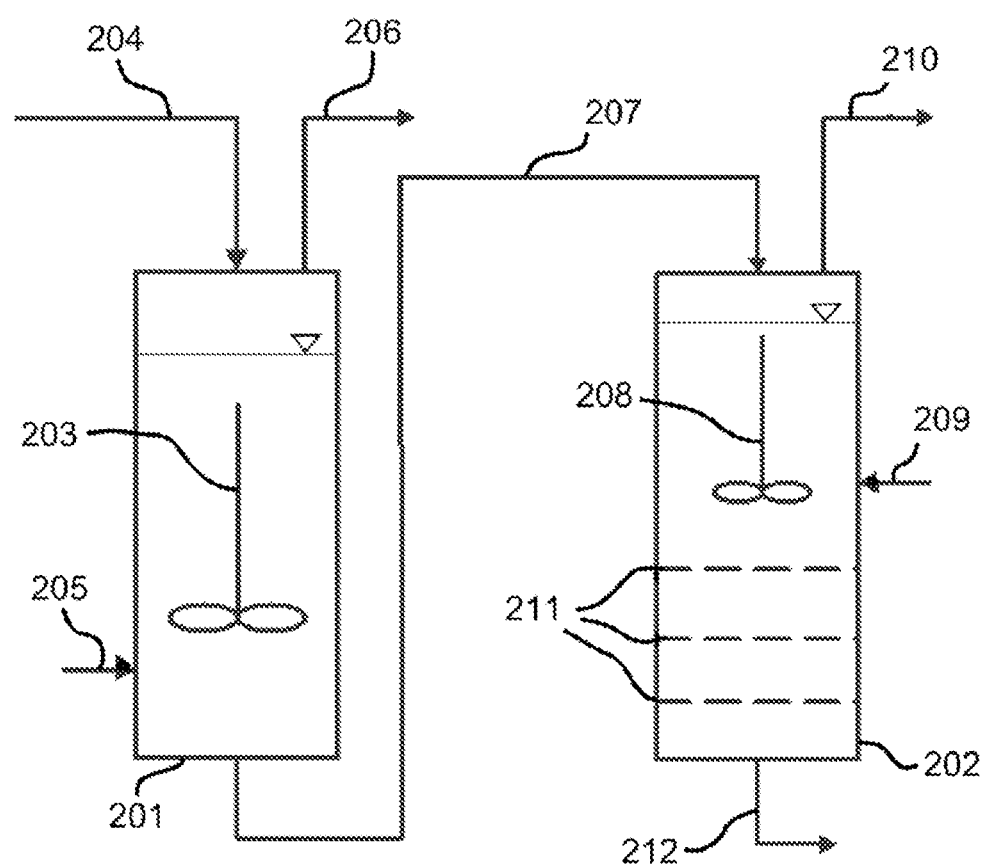
FIG. 2 shows a schematic representation of a system suitable for executing the process of the invention.

According to FIG. 2, a system suitable for executing the process of the invention comprises a first hydrogenation reactor 201 and a second hydrogenation reactor 202.

The hydrogenation reactor 201 comprises a stirrer 203. A liquid comprising a reactant to be hydrogenated is supplied to the hydrogenation reactor 201 via line 204. Hydrogen gas is supplied to the hydrogenation reactor 201 via line 205. The offgas from the hydrogenation reactor 201 is conducted out of the hydrogenation reactor 1 via line 206.

The outflow stream 207 conducted out at the bottom of the hydrogenation reactor 201 is supplied to the hydrogenation reactor 202. The hydrogenation reactor 202 comprises a stirrer 208. Hydrogen gas is supplied to the hydrogenation reactor 202 via line 209. The offgas from the hydrogenation reactor 202 is conducted out of the hydrogenation reactor 202 via line 210.

The hydrogenation reactor 202 comprises fitted trays 211 that limit backmixing in the hydrogenation reactor 202. The trays are preferably perforated sheets. Dispersed hydrogen gas is at least partially retained by the trays, with the result that the proportion of dispersed gas in the liquid reaction mixture in the section located at the exit from the second reactor decreases. At the exit at least, the hydrogenation takes place in liquid single-phase.

A liquid comprising the hydrogenated reaction product is conducted out of the hydrogenation reactor 202 via line 212.

A liquid comprising a homogeneous rhodium catalyst that has at least one chiral ligand is metered into the liquid stream 204 (not shown).

Figure 3:
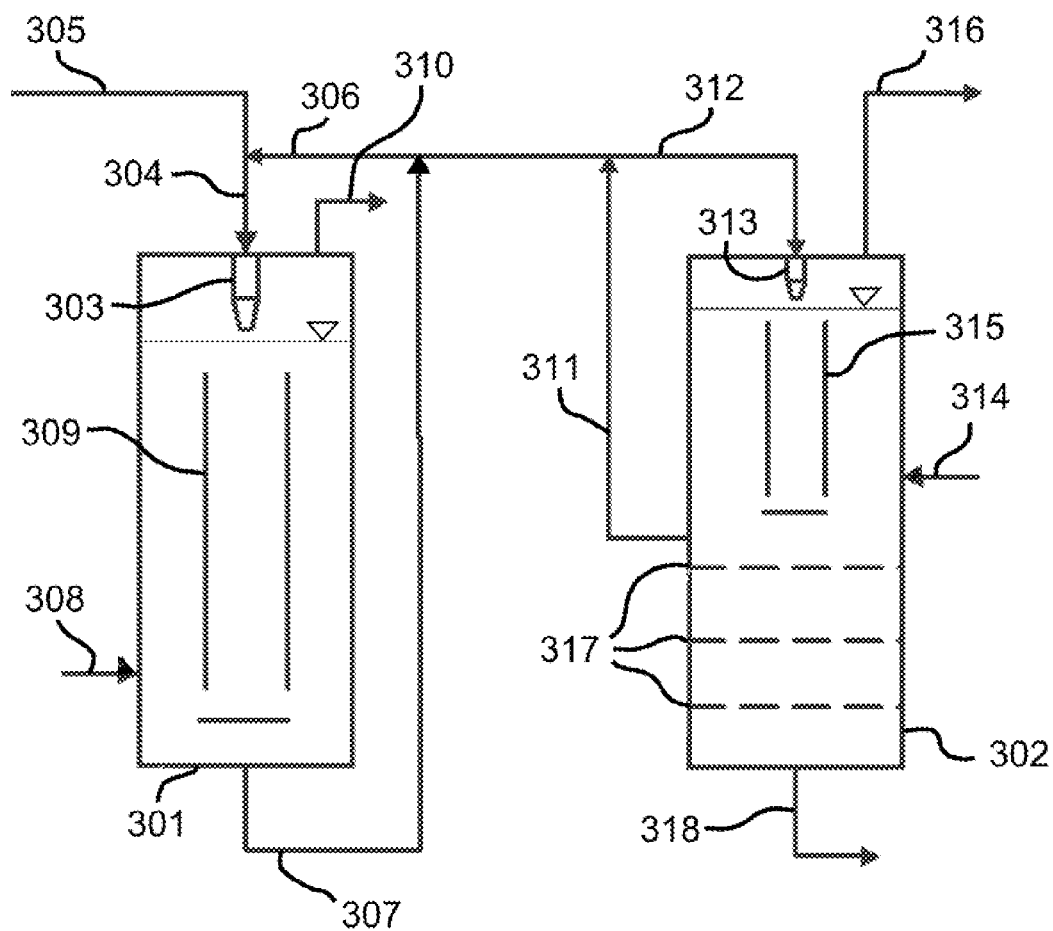
FIG. 3 shows a schematic representation of a system suitable for executing the process of the invention.

According to FIG. 3, a system suitable for executing the process of the invention comprises a first hydrogenation reactor 301 and a second hydrogenation reactor 302.

The hydrogenation reactors 301 and 302 are mixed by injection and each has a pumped-circulation circuit.

The hydrogenation reactor 301 comprises a jet nozzle 303. A liquid is supplied from line 304 to the hydrogenation reactor 301 via the jet nozzle 303. The liquid stream from line 304 comprises the reactant stream 305 and the pumped-circulation stream 306. The reactant stream 305 comprises a liquid comprising a reactant to be hydrogenated. The pumped-circulation stream 306 is a substream of the outflow stream 307 conducted out at the bottom of the hydrogenation reactor 1. Hydrogen gas is supplied to the hydrogenation reactor 301 via line 308. The hydrogenation reactor 301 comprises a guide tube 309, the jet nozzle 303 being arranged above the level of the liquid and the gas/liquid jet generated by the jet nozzle 303 being directed into the guide tube 309. The offgas from the hydrogenation reactor 301 is conducted out of the hydrogenation reactor 301 via line 310.

A substream of the outflow stream 307 is combined with the liquid pumped-circulation stream 311 withdrawn from the backmixed zone of the hydrogenation reactor 302 to form liquid stream 312 and supplied to the hydrogenation reactor 302 via the jet nozzle 313. Hydrogen gas is supplied to the hydrogenation reactor 302 via line 314. The hydrogenation reactor 302 comprises a guide tube 315, the jet nozzle 313 being arranged above the level of the liquid and the gas/liquid jet generated by the jet nozzle 313 being directed into the guide tube 315. The offgas from the hydrogenation reactor 302 is conducted out of the hydrogenation reactor 302 via line 316.

The hydrogenation reactor 302 comprises fitted trays 317 that limit backmixing in the hydrogenation reactor 302. The trays are preferably perforated sheets. Dispersed hydrogen gas is at least partially retained by the trays, with the result that the proportion of dispersed gas in the liquid reaction mixture in the section located at the exit from the second reactor decreases. At the exit at least, the hydrogenation takes place in liquid single-phase.

A liquid comprising the hydrogenated reaction product is conducted out of the hydrogenation reactor 302 via line 318.

A liquid comprising a homogeneous rhodium catalyst that has at least one chiral ligand is metered into the pumped-circulation circuit of the hydrogenation reactor 301, for example into the liquid stream 304 (not shown). The pumped-circulation circuit of the hydrogenation reactor 301 and of the hydrogenation reactor 302 comprises an external heat exchanger (not shown) that for example cools the outflow stream 307 and the pumped-circulation stream 311.

EXAMPLE 1500 kg/h of citral and 1500 kg/h of a catalyst mixture were fed into a jet loop reactor having a liquid volume of 12 m$^3$. The catalyst mixture was a mixture prepared in analogous manner to the procedures described in US 2018/057437 A1, WO 2006/040096, and WO 2008/132057 A1, in which Rh(CO)$_2$acac, chiraphos, and tridodecylamine in a molar ratio of 1:1.4:10 were reacted with CO and H$_2$ in citronellal. The concentration of the catalyst mixture in the jet loop reactor was 300 to 1000 ppm by weight based on the amount of rhodium in the catalyst. The ratio of external circulation to feed was 380:130. The ratio of internal circulation to feed was 3000:1000.

The power input was 2 kW/m$^3$. The pressure in the reactor was regulated to 80 bar by feeding in hydrogen gas (containing 1000 ppm of carbon monoxide). The temperature in the reactor was regulated to 22° C. Conversion of the citral was 88%. A citral concentration of about 7% by weight was present in the outflow from the first reactor.

The outflow from the reactor was fed into a second reactor having a liquid volume of 9.7 m$^3$. The pressure in the second reactor was regulated to 80 bar by feeding in hydrogen gas (containing 1000 ppm of carbon monoxide). The temperature in the reactor was regulated to 22° C. The total conversion after the second reactor was between 93 and 99.9%.

It was found that the reaction rate in the first reactor decreased at higher citral concentrations. It thus proved advantageous to operate the first reactor at low citral concentrations and to complete the reaction in the second reactor.

The invention claimed is:

1. A process for the continuous production of an optically active carbonyl compound by asymmetric hydrogenation of a prochiral α,β-unsaturated carbonyl compound with hydrogen in the presence of a homogeneous rhodium catalyst that has at least one chiral ligand, wherein
   a liquid reaction mixture comprising the prochiral α,β-unsaturated carbonyl compound is subjected in a first, backmixed reactor to a gas/liquid two-phase hydrogenation, and
   the liquid reaction mixture is then further hydrogenated in a second reactor,
   wherein the prochiral α,β-unsaturated carbonyl compound is employed in the first reactor in a concentration from 3% to 20% by weight.

2. The process according to claim 1, wherein hydrogen gas undergoes dispersion in the liquid reaction mixture in a section of the second reactor located at the entrance to the second reactor.

3. The process according to claim 1, wherein the prochiral α,β-unsaturated carbonyl compound is employed in the first reactor in a concentration at which the reaction rate is at least 0.8 times $V_{max}$, $V_{max}$ being the maximum value for the reaction rate in a plot of the reaction rate against the concentration of the prochiral α,β-unsaturated carbonyl compound.

4. The process according to claim 1, wherein the liquid reaction mixture undergoes reaction in the second reactor until the concentration of the prochiral α,β-unsaturated carbonyl compound is less than 5% by weight.

5. The process according to claim 1, wherein the ratio of the reaction volume of the first reactor to the reaction volume of the second reactor is 1:1 to 1:5.

6. The process according to claim 1, wherein the first reactor is characterized by a reactor number N within a range from 1 to 3.

7. The process according to claim 1, wherein the volume-specific power input into the first reactor is 0.5 to 5 kW/m$^3$.

8. The process according to claim 1, wherein the first reactor is configured as a loop reactor.

9. The process according to claim 1, wherein backmixing in the second reactor is limited and wherein, at least in a section of the second reactor located at the exit from the second reactor, the hydrogenation is carried out in liquid single-phase.

10. The process according to claim 9, wherein backmixing in the second reactor is limited by internals.

11. The process according to claim 1, wherein the second reactor is characterized by a reactor number N of more than 4.

12. The process according to claim 1, wherein the prochiral α,β-unsaturated carbonyl compound is selected from compounds of the general formula (I)

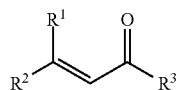
(I)

where
R$^1$, R$^2$ are different from one another and are each an unbranched, branched or cyclic hydrocarbon radical having 1 to 25 carbon atoms that is saturated or has one or more unconjugated ethylenic double bonds and that is unsubstituted or bears one or more identical or different substituents selected from OR$^4$, NR$^{5a}$R$^{5b}$, halogen, C$_6$-C$_{10}$ aryl and heteroaryl having 5 to 10 ring atoms, R$^3$ is hydrogen or an unbranched, branched or cyclic hydrocarbon radical having 1 to 25 carbon atoms that is saturated or has one or more unconjugated ethylenic double bonds and that is unsubstituted or bears one or more identical or different substituents selected from OR$^4$, NR$^{5a}$R$^{5b}$, halogen, C$_6$-C$_{10}$ aryl and heteroaryl having 5 to 10 ring atoms, or R$^3$ jointly with either of the radicals R$^1$ or R$^2$ may also represent a 3- to 25-membered alkylene group wherein 1, 2, 3 or 4 nonadjacent CH$_2$-groups may be replaced by O or N—R$^{5c}$, wherein the alkylene group is saturated or has one or more unconjugated ethylenic double bonds and wherein the alkylene group is unsubstituted or bears one or more identical or different substituents selected from OR$^4$, NR$^{5a}$R$^{5b}$, halogen, C$_1$-C$_4$-alkyl, C$_6$-C$_{10}$-aryl and heteroaryl having 5 to 10 ring atoms, wherein two substituents may also jointly represent a 2- to 10-membered alkylene group, wherein the 2- to 10-membered alkylene group is saturated or has one or more unconjugated ethylenic double bonds and wherein the 2- to 10-membered alkylene group is unsubstituted or bears one or more identical or different substituents selected from OR$^4$, NR$^{5a}$R$^{5b}$, halogen, C$_6$-C$_{10}$-aryl and heteroaryl having 5 to 10 ring atoms;

where

R$^4$ is hydrogen, C$_1$-C$_6$ alkyl, C$_6$-C$_{10}$ aryl, C$_6$-C$_{14}$ aryl-C$_1$-C$_{10}$ alkyl, or C$_1$-C$_{10}$ alkyl-C$_6$-C$_{14}$ aryl;

R$^{5a}$, R$^{5b}$ are each independently hydrogen, C$_1$-C$_6$ alkyl, C$_6$-C$_{10}$ aryl, C$_6$-C$_{14}$ aryl-C$_1$-C$_{10}$ alkyl or C$_1$-C$_{10}$ alkyl-C$_6$-C$_{14}$ aryl or R$^{5a}$ and R$^{5b}$ may also jointly represent an alkylene chain having 2 to 5 carbon atoms, which may be interrupted by N or O; and R$^{5c}$ is hydrogen, C$_1$-C$_6$ alkyl, C$_6$-C$_{10}$ aryl, C$_6$-C$_{14}$ aryl-C$_1$-C$_{10}$ alkyl, or C$_1$-C$_{10}$ alkyl-C$_6$-C$_{14}$ aryl.

13. The process according to claim 12 for producing optically active citronellal of the formula (III)

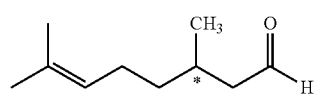
(III)

where * denotes the asymmetric center;
by asymmetric hydrogenation of geranial of the formula (Ia-1) or of neral of the formula (Ib-1)

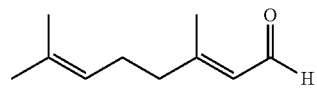
(Ia-1)

(Ib-1)

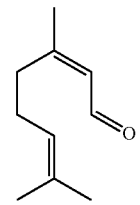

or of a mixture comprising neral and geranial.

14. The process according to claim 1, wherein the catalyst concentration is 0.001 to 1 mol % based on the amount of prochiral α,β-unsaturated carbonyl compound in the reaction mixture calculated as rhodium atoms present in the catalyst.

15. The process according to claim 1, wherein the chiral ligand is a chiral bidentate bisphosphine ligand.

16. The process according to claim 1, wherein the process is executed in the presence of a compound of the formula (II),

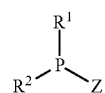
(II)

where Z in the formula (II) is a CHR$^3$R$^4$ group and where the variables R$^1$, R$^2$, R$^3$, R$^4$ are independently as follows:

R$^1$, R$^2$: are identical or different and are phenyl that is unsubstituted or bears 1, 2 or 3 substituents selected from methyl and methoxy;

R$^3$ is C$_1$ to C$_4$ alkyl;

R$^4$ is C$_1$ to C$_4$ alkyl bearing a P(=O)R$^{4a}$R$^{4b}$ group;

where

R$^{4a}$, R$^{4b}$: are identical or different and are phenyl that is unsubstituted or bears 1, 2 or 3 substituents selected from methyl and methoxy.

17. A process for producing optically active menthol in which optically active citronellal of the formula (III) is produced in the process according to claim 13 in which the optically active citronellal of the formula (III) is subjected to a cyclization to afford optically active isopulegol and the optically active isopulegol is hydrogenated to afford optically active menthol.

18. The process according to claim 15, wherein the chiral ligand is chiraphos.

19. The process according to claim 16, wherein:
R$^1$ and R$^2$ are each unsubstituted phenyl;
R$^3$ is methyl;
R$^4$ is a CH$_2$—P(=O)R$^{4a}$R$^{4b}$ or CH(CH$_3$)—P(=O)R$^{4a}$R$^{4b}$ group; and
R$^{4a}$ and R$^{4b}$ are each unsubstituted phenyl.

* * * * *